(12) United States Patent
Chatterjee et al.

(10) Patent No.: US 11,885,862 B2
(45) Date of Patent: Jan. 30, 2024

(54) DEEP LEARNING BASED MAGNETIC RESONANCE IMAGING (MRI) EXAMINATION ACCELERATION

(71) Applicant: GE Precision Healthcare LLC, Wauwatosa, WI (US)

(72) Inventors: Sudhanya Chatterjee, Bangalore (IN); Dattesh Shanbhag, Bangalore (IN); Suresh Joel, Bangalore (IN)

(73) Assignee: GE Precision Healthcare LLC, Wauwatosa, WI (US)

( * ) Notice: Subject to any disclaimer, the term of this patent is extended or adjusted under 35 U.S.C. 154(b) by 480 days.

(21) Appl. No.: 17/083,074

(22) Filed: Oct. 28, 2020

(65) Prior Publication Data

US 2022/0128640 A1 Apr. 28, 2022

(51) Int. Cl.
*G01R 33/56* (2006.01)
*A61B 5/055* (2006.01)
*G06T 7/00* (2017.01)
*G01R 33/48* (2006.01)
*G01R 33/483* (2006.01)
*G06F 18/22* (2023.01)

(52) U.S. Cl.
CPC .......... *G01R 33/5608* (2013.01); *A61B 5/055* (2013.01); *G01R 33/4818* (2013.01); *G01R 33/4835* (2013.01); *G06F 18/22* (2023.01); *G06T 7/0012* (2013.01); *G06T 2207/10088* (2013.01); *G06T 2207/20081* (2013.01); *G06T 2207/20084* (2013.01)

(58) Field of Classification Search
None
See application file for complete search history.

(56) References Cited

U.S. PATENT DOCUMENTS

| 2017/0212196 A1* | 7/2017 | Feiweier | G01R 33/385 |
| 2017/0254869 A1* | 9/2017 | Miyazaki | G01R 33/56509 |
| 2020/0011951 A1* | 1/2020 | Shi | G01R 33/56536 |
| 2020/0041592 A1 | 2/2020 | Huang | |
| 2020/0202586 A1 | 6/2020 | Li | |

OTHER PUBLICATIONS

Wang, Shanshan, et al. "Accelerating magnetic resonance imaging via deep learning." 2016 IEEE 13th international symposium on biomedical imaging (ISBI). IEEE, 2016. (Year: 2016).*

(Continued)

*Primary Examiner* — Samah A Beg

(57) ABSTRACT

Systems and methods for deep learning based magnetic resonance imaging (MRI) examination acceleration are provided. The method of deep learning (DL) based magnetic resonance imaging (MRI) examination acceleration comprises acquiring at least one fully sampled reference k-space data of a subject and acquiring a plurality of partial k-space of the subject. The method further comprises grafting the plurality of partial k-space with the at least one fully sampled reference k-space data to generate a grafted k-space for accelerated examination. The method further comprises training a deep learning (DL) module using the fully sampled reference k-space data and the grafted k-space to remove the grafting artifacts.

21 Claims, 9 Drawing Sheets

(56) References Cited

OTHER PUBLICATIONS

Hammernik, Kerstin, et al. "Learning a variational network for reconstruction of accelerated MRI data." Magnetic resonance in medicine 79.6 (2018): 3055-3071. (Year: 2018).*

Hammernik et al., "Learning a Variational Network for Reconstruction of Accelerated MRI Data," 24th Annual Meeting of ISMRM, Singapore, 2016, published Nov. 8, 2017, 29 pages.

Yan et al., "Data truncation artifact reduction in MR imaging using a multilayer neural network," IEEE Transactions on Medical Imaging; vol. 12, Issue: 1; Mar. 1993, 5 pages.

* cited by examiner

DEEP LEARNING BASED MAGNETIC RESONANCE IMAGING (MRI) EXAMINATION ACCELERATION

FIELD OF THE INVENTION

Embodiments of the present disclosure relate generally to improved imaging systems and more particularly to deep learning based magnetic resonance imaging (MRI) examination acceleration.

BACKGROUND OF THE INVENTION

Magnetic resonance imaging (MRI) systems are used in the field of medical imaging to acquire image data of the anatomical parts of the subject human body (hereinafter subject). Several image processing techniques are commercially available to generate the images with improved quality from the image data acquired by the MRI systems. Although the images produced by these image processing techniques are of good quality, many images are adversely affected by the operational conditions of the MRI system and subject movement.

Imaging artifacts or MRI artifacts are imaging defects produced during scanning that adversely affect the image quality. These artifacts are typically produced by movement of the subject or subject organs such as heart, lungs, blood vessels during imaging. These artifacts are called motion artifacts. Also, the subsequent images obtained during the long MRI scans may differ from the previous images of the same subject due to movement of the subject organs. These and other defects pose a challenge during the analysis of the images by the radiologist.

Different image acquisition and processing techniques are known in the art to minimize the artifacts. Accelerating the MRI examinations is a technique that has shown substantive improvement in image artifacts. Scan time reduction in the MRI examinations have been predominantly focused on accelerating each contrast from the different images obtained during scanning. In current approaches, the MRI acceleration is obtained by under sampling the raw data space and sharing information from another protocol (or contrast) acquisition in same sitting. The MRI images reconstructed by the techniques such as zero filled and compressed sensing have defects like structural artifacts, missing structures and blurring.

Among different approaches to improve the image quality, Deep Learning (DL) algorithms are trained algorithms used in the field of medical imaging for computer assisted detection and diagnosis of the medical condition of the subject. DL modules containing DL algorithms are usually trained with several MRI images and subsequent MRI images of the subject may be analyzed using the DL modules to recognize the image patterns. The artifacts such as missing structures and blurring may not be overcome by the presently available deep learning (DL) techniques. In cases where the deep learning (DL) technique overcomes these artifacts, it is due to the data synthesis by the DL modules and not due to the artifact removal.

Existing techniques take a long time for multi-contrast MR examination and does not use data redundancy by efficient processing. What is required is an MRI examination acceleration technique that will provide high-resolution images for multiple contrasts in single examination quickly.

BRIEF DESCRIPTION OF THE INVENTION

This summary introduces concepts that are described in more detail in the detailed description. It should not be used to identify essential features of the claimed subject matter, nor to limit the scope of the claimed subject matter. Its sole purpose is to present concepts in a simplified form as a prelude to the more detailed description that is presented later.

In accordance with one aspect of the disclosure, a method for magnetic resonance imaging (MRI) examination acceleration is provided. The method comprises acquiring at least one fully sampled reference k-space data of a subject and acquiring a plurality of partial k-space of the subject. The method further comprises grafting the plurality of partial k-space with the at least one fully sampled reference k-space data to generate a grafted k-space for accelerated examination.

In accordance with another aspect of the disclosure, a method for deep learning (DL) based magnetic resonance imaging (MRI) examination acceleration is provided. The method comprises acquiring at least one fully sampled reference k-space data of a subject and acquiring a plurality of partial k-space of the subject. The method further comprises grafting the partial k-space of the subject with the fully sampled reference k-space data to generate a grafted k-space for accelerated examination. The method further comprises training a deep learning (DL) module using the fully sampled reference k-space data and the grafted k-space to predict and remove the grafting artifacts.

In accordance with another aspect of the disclosure a magnetic resonance imaging (MRI) system is provided. The magnetic resonance imaging (MRI) system comprises at least one radiofrequency (RF) body coil adapted to transmit and receive radiofrequency (RF) signals to and from a subject. The MRI system further comprises a transceiver module configured to digitize the signals received by the radiofrequency (RF) body coil. The MRI system further comprises a control system configured to process the digitized signals and generate k-space data corresponding to an imaged volume of the subject, wherein the MRI system is configured to acquire at least one fully sampled reference k-space data of the subject and a plurality of partial k-space of the subject. The MRI system further comprises a computer processor configured to graft the partial k-space with the fully sampled reference k-space data to generate a grafted k-space for accelerated examination.

BRIEF DESCRIPTION OF THE DRAWINGS OF THE INVENTION

These and other features of the embodiments of the present disclosure will be better understood when the following non-limiting embodiments in the detailed description are read with reference to the accompanying drawings, wherein below:

DETAILED DESCRIPTION

The following detailed description of the exemplary embodiments refers to the accompanying drawings. The same reference numbers in different drawings identify the same or similar elements. Additionally, the drawings are not necessarily drawn to scale. Also, the following detailed description does not limit the invention. Instead, the scope of the invention is defined by the appended claims.

Reference throughout the specification to "one embodiment" or "another embodiment" or "some embodiments" means that the feature, structure or characteristic described in connection with an embodiment is included in at least one embodiment of the subject matter disclosed. Thus, the appearance of the phrase "in one embodiment" or "in an embodiment" or "in some embodiments" in various places throughout the specification is not necessarily referring to the same embodiment(s). Further, the features, structures or characteristics may be combined in any suitable manner in one or more embodiments.

Present disclosure provides a method of deep learning (DL) based magnetic resonance imaging (MRI) examination acceleration. The method comprises acquiring at least one fully sampled reference k-space data of a subject and acquiring a plurality of partial k-space of the subject. The method further comprises grafting the partial k-space with the fully sampled reference k-space data to generate a grafted k-space for accelerated examination. The method further comprises training a deep learning (DL) module using the fully sampled reference k-space data and the grafted k-space to predict and remove the grafting artifacts.

Medical imaging devices such as magnetic resonance imaging (MRI) systems generate images representative of the parts of the body (e.g., organs, tissues) to diagnose and treat the diseases. Transmission, acquisition, processing, analysis, and storage of the medical image data plays an important role in the diagnosis and treatment of the patients in healthcare.

Figure 1:
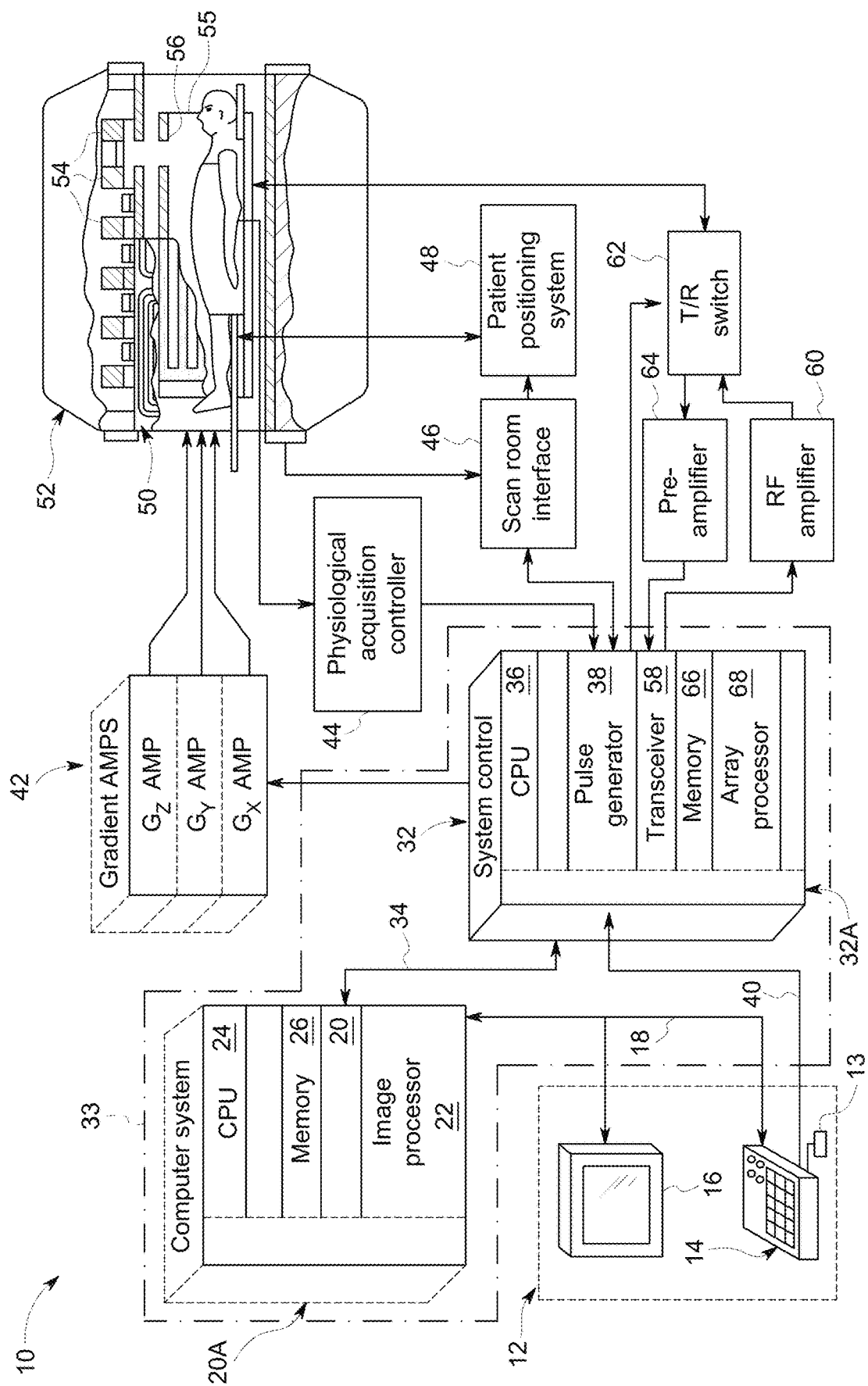
FIG. 1 illustrates an example implementation of a magnetic resonance imaging (MRI) system according to an aspect of the disclosure.

The methods, apparatus, and articles of manufacture described herein may be applied to a variety of healthcare and non-healthcare systems. In one example, the methods, apparatus, and articles of manufacture described herein may be applied to the components, configuration, and operation of a magnetic resonance imaging (MRI) system. FIG. 1 illustrates an example implementation of a magnetic resonance imaging (MRI) system to which the methods, apparatus, and articles of manufacture disclosed herein may be applied.

Embodiments of the present disclosure will now be described, by way of an example, with reference to the figures, in which FIG. 1 is a schematic diagram of a magnetic resonance imaging (MRI) system (10). Operation of the system (10) may be controlled from an operator console (12), which includes an input device (13), a control panel (14), and a display screen (16). The input device (13) may be a mouse, joystick, keyboard, track ball, touch activated screen, light wand, voice control, and/or other input device. The input device (13) may be used for interactive geometry prescription. The console (12) communicates through a link (18) with a computer system (20) that enables an operator to control the production and display of images on the display screen (16). The link (18) may be a wireless or wired connection. The computer system (20) may include modules that communicate with each other through a backplane (20a). The modules of the computer system (20) may include an image processor module (22), a central processing unit (CPU) module (24), and a memory module (26) that may include a frame buffer for storing image data arrays, for example. The computer system (20) may be linked to archival media devices, permanent or back-up memory storage or a network for storage of image data and programs and communicates with MRI system control (32) through a high-speed signal link (34). The MRI system control (32) may be separate from or integral with the computer system (20). The computer system (20) and the MRI system control (32) collectively form an "MRI controller" (33) or "controller".

In the exemplary embodiment, the MRI system control (32) includes modules connected by a backplane (32a). These modules include a CPU module (36) as well as a pulse generator module (38). The CPU module (36) connects to the operator console (12) through a data link (40). The MRI system control (32) receives commands from the operator through the data link (40) to indicate the scan sequence that is to be performed. The CPU module (36) operates the system components to carry out the desired scan sequence and produces data which indicates the timing, strength and shape of the RF pulses produced, and the timing and length of the data acquisition window. The CPU module (36) connects to components that are operated by the MRI controller (32), including the pulse generator module (38) which controls a gradient amplifier (42), a physiological acquisition controller (PAC) (44), and a scan room interface circuit (46).

In one example, the CPU module (36) receives patient data from the physiological acquisition controller (44), which receives signals from sensors connected to the subject, such as ECG signals received from electrodes attached to the patient. The CPU module (36) receives, via the scan room interface circuit (46), signals from the sensors associated with the condition of the patient and the magnet system. The scan room interface circuit (46) also enables the MRI controller (33) to command a patient positioning system (48) to move the patient to a desired position for scanning.

A whole-body RF coil (56) is used for transmitting the waveform towards subject anatomy. The whole body-RF coil (56) may be a body coil (as shown in FIG. 1). An RF coil may also be a local coil that may be placed in more proximity to the subject anatomy than a body coil. The RF coil (56) may be a surface coil. Surface coil containing receiving channels may be used for receiving the signals from the subject anatomy. Typical surface coil would have eight receiving channels; however, different number of channels are possible. Using the combination of both a body coil (56) and a surface coil is known to provide better image quality.

The pulse generator module (38) may operate the gradient amplifiers (42) to achieve desired timing and shape of the gradient pulses that are produced during the scan. The gradient waveforms produced by the pulse generator module

(38) may be applied to the gradient amplifier system (42) having Gx, Gy, and Gz amplifiers. Each gradient amplifier excites a corresponding physical gradient coil in a gradient coil assembly (50), to produce the magnetic field gradients used for spatially encoding acquired signals. The gradient coil assembly (50) may form part of a magnet assembly (52), which also includes a polarizing magnet (54) (which, in operation, provides a longitudinal magnetic field B0 throughout a target volume (55) that is enclosed by the magnet assembly 52) and a whole-body RF coil (56) (which, in operation, provides a transverse magnetic field B1 that is generally perpendicular to B0 throughout the target volume 55). A transceiver module (58) in the MRI system control (32) produces pulses that may be amplified by an RF amplifier (60) and coupled to the RF coil (56) by a transmit/receive switch (62). The resulting signals emitted by the excited nuclei in the subject anatomy may be sensed by receiving coils (not shown) and provided to a preamplifier (64) through the transmit/receive switch (62). The amplified MR signals are demodulated, filtered, and digitized in the receiver section of the transceiver (58). The transmit/receive switch (62) is controlled by a signal from the pulse generator module (38) to electrically connect the RF amplifier (60) to the coil (56) during the transmit mode and to connect the preamplifier (64) to the receiving coil during the receive mode.

The MR signals produced from excitation of the target are digitized by the transceiver module (58). The MR system control (32) then processes the digitized signals by Fourier transform to produce k-space data, which is transferred to a memory module (66), or other computer readable media, via the MRI system control (32). "Computer readable media" may include, for example, structures configured so that electrical, optical, or magnetic states may be fixed in a manner perceptible and reproducible by a conventional computer (e.g., text or images printed to paper or displayed on a screen, optical discs, or other optical storage media, "flash" memory, EEPROM, SDRAM, or other electrical storage media; floppy or other magnetic discs, magnetic tape, or other magnetic storage media).

A scan is complete when an array of raw k-space data has been acquired in the computer readable media (66). This raw k-space data is rearranged into separate k-space data arrays for each image to be reconstructed, and each of these k-space data arrays is input to an array processor (68), which operates to reconstruct the data into an array of image data, using a reconstruction algorithm such as a Fourier transform. When the full k-space data is obtained, it represents entire volume of the subject body and the k-space so obtained may be referred as the reference k-space. Similarly, when only the central k-space data is obtained, the image may be referred as the central k-space. This image data is conveyed through the data link (34) to the computer system (20) and stored in memory. In response to the commands received from the operator console (12), this image data may be archived in a long-term storage or may be further processed by the image processor (22) and conveyed to the operator console (12) and presented on the display (16).

Figure 2:
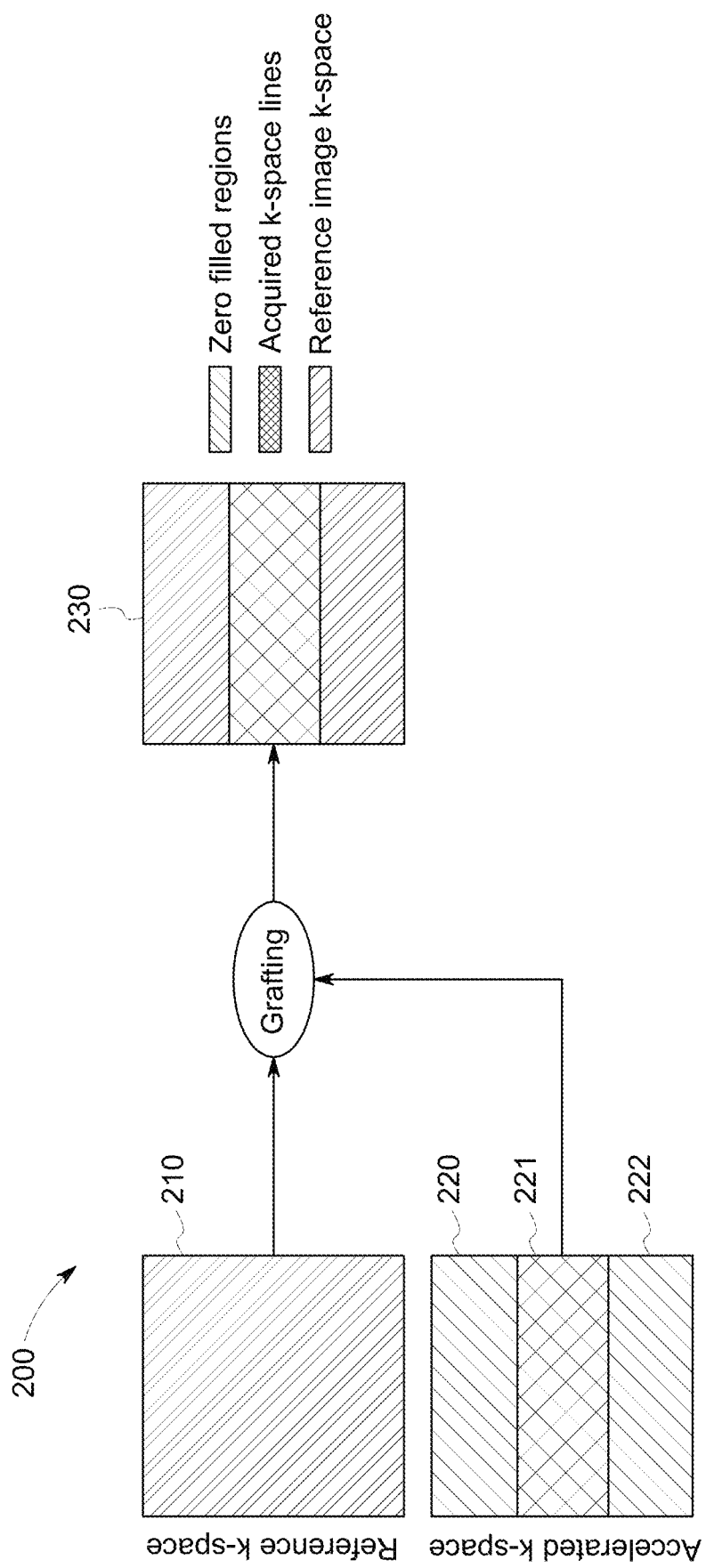
FIG. 2 illustrates a method of k-space grafting for accelerated MRI image examination according to an aspect of the disclosure.

In accordance with an aspect of the disclosure, FIG. 2 shows a method (200) of grafting the partial k-space (220) with the fully sampled reference k-space data (210) to obtain an accelerated image (230). Duration of the MRI scans may extend from few minutes to several minutes. As the MRI scans involve acquisition of entire k-space (210) during each scan, acquiring the images in minimum time is critical for accelerated examination. According to an aspect of the disclosure, the k-space (220) may be divided into the central portion (221) of the k-space (220) and the peripheral portion (222) of the k-space (220). Among the image parameters, the central portion (221) of the k-space determines the image contrast and the brightness of the image; and the peripheral portion (222) of the k-space determines the quality of the edge of the image (220). Traditionally, the MRI examination consists of acquiring the multiple contrasts or the images (220) of the subject and accelerating the MRI examination has been focused on accelerating each contrast.

According to an aspect of the disclosure, a fully sampled reference k-space data (210) may be obtained at the beginning of the scan. Acquisition of the reference data may include acquisition of the entire k-space (210). This fully sampled reference k-space data (210) may be stored for future reference and used across the scans. This is also known as the fully sampled image (210). Acquisition time of the fully sampled reference k-space data (210) needs to be reduced for faster imaging. For accelerated examination, only the partial k-space (221) or the central portion of the k-space that represents only a part of the entire k-space (220) may be acquired instead of acquiring the complete k-space (220). Acquiring only the partial k-space (221) instead of entire k-space (220) during the subsequent scanning accelerates the image acquisition process. The partial k-space (221) acquired during the subsequent scans may be grafted with the outer k-space of the fully sampled reference data (210). In this manner, the structural information from the reference k-space data (210) may be shared during the further stages of the MRI examination without compromising the contrast. By way of grafting the partial k-space (221) with the outer k-space from the reference data (210), a complete k-space data (230) may be obtained. Grafting of the partial k-space (221) with the reference outer k-space data (210) provides accelerated examination that increases the scan throughput and reduces the artifacts during the longer scans.

Figure 3:
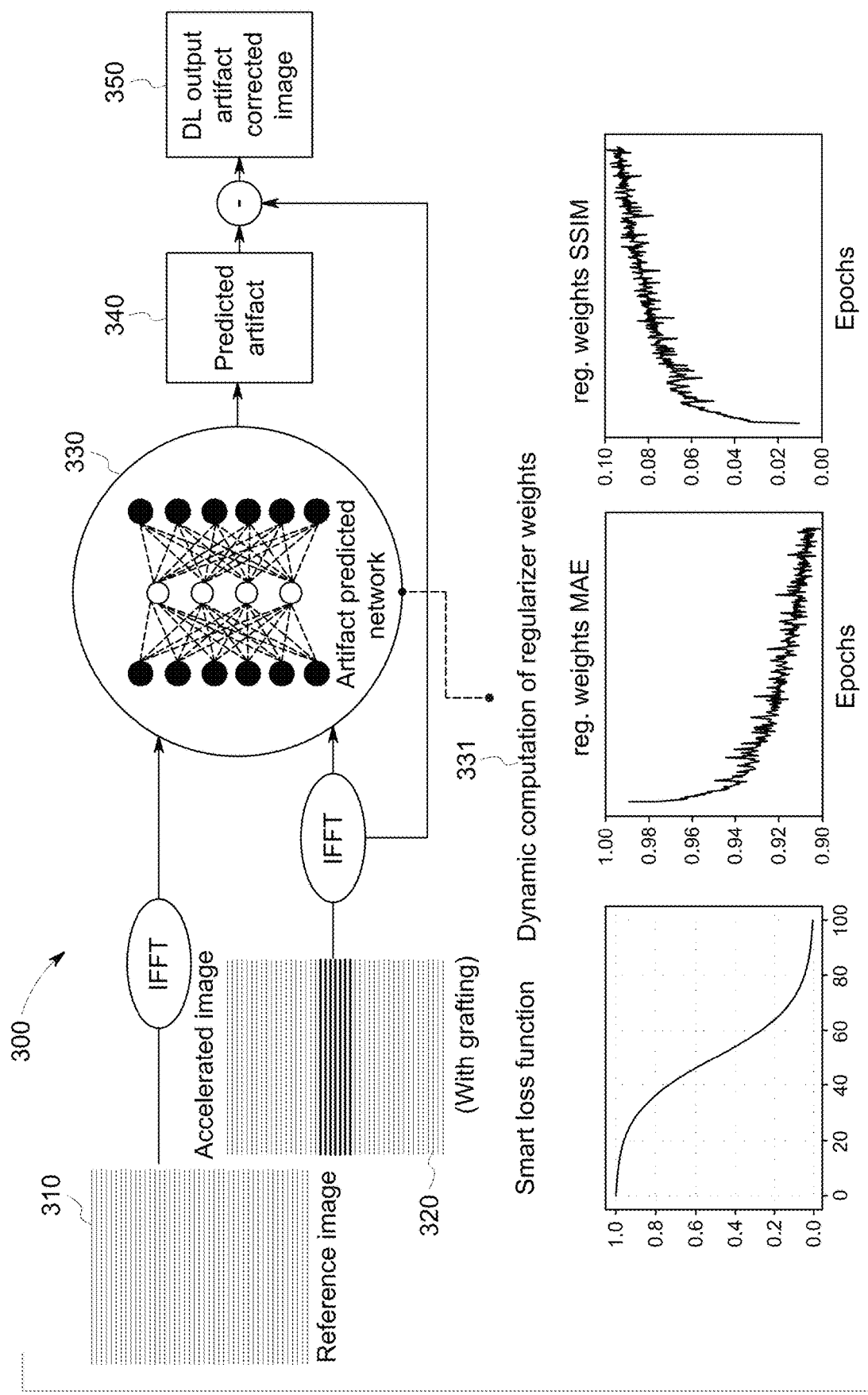
FIG. 3 illustrates a method of artifact correction of the MRI images according to an aspect of the disclosure.

According to an aspect of the disclosure as shown in FIG. 3, a method (300) of artifact correction of the MRI images is disclosed. The operation of the grafting may be employed before processing the k-space data by a deep learning (DL) module. Grafting process may generate the artifacts such as sharp high frequency artifacts that may be removed using a deep learning network according to an aspect of the disclosure.

Deep learning is a class of machine learning techniques employing representation learning methods that allows a machine to be given raw data and determine the representations needed for data classification. Deep learning ascertains structure in data sets using backpropagation algorithms. Deep learning machines may utilize a variety of multilayer architectures and algorithms. While machine learning, for example, involves an identification of features to be used in training the network, deep learning may process raw data to identify features of interest without the external identification.

Deep learning in a neural network environment includes numerous interconnected nodes referred to as neurons. Input neurons, activated from an outside source, activate other neurons based on connections to these other neurons which are governed by the machine operating conditions. A neural network behaves in a certain manner based on its own sequences. Learning refines the machine output, and the connections between neurons in the network such that the neural network behaves in a desired manner.

Deep learning that utilizes a convolutional neural network segments data using convolutional filters to locate and identify learned, observable features in the data. Each filter or layer of the CNN architecture transforms the input data to increase the selectivity and invariance of the data. This abstraction of the data allows the machine to focus on the features in the data that the machine attempts to classify and ignore irrelevant background information.

Deep learning operates on the understanding that many datasets include high level features and low-level features. At high level, while examining an image, for example, rather than looking for an object, it is more efficient to look for edges which form motifs which form parts, which form the object being sought. These hierarchies of features may be found in many different forms of data such as speech and text.

Learned observable features include objects and quantifiable regularities learned by the machine during supervised learning. A machine provided with a large set of well classified data is better equipped to distinguish and extract the features in successful classification of new data than the traditional algorithms that are not continuously trained to classify the data.

A deep learning machine that utilizes transfer learning may properly connect data features to certain classifications affirmed by a human expert. Conversely, the same machine may, when informed of an incorrect classification by a human expert, update the system for classification. Settings and/or other configuration information, for example, may be guided by learned use of settings and/or other configuration information, and, as a system is used more (e.g., repeatedly and/or by multiple users), a number of variations and/or other possibilities for settings and/or other configuration information may be reduced for a given situation.

An example deep learning neural network may be trained on a set of expert classified data, for example. This set of data builds the neural network and is the stage of supervised learning. During the stage of supervised learning, the neural network may be tested whether the desired behavior has been achieved.

Once a desired neural network behavior has been achieved (e.g., a machine has been trained to operate according to a specified threshold, etc.), the machine may be deployed for use (e.g., testing the machine with "real" data, etc.). During operation, neural network classifications may be confirmed or denied (e.g., by an expert user, expert system, reference database, etc.) to continue improving neural network behavior. The example neural network is then in a state of transfer learning, as conditions for classification that determine neural network behavior are updated based on ongoing interactions. In certain examples, the neural network may provide direct feedback to other examination processes of the patient in healthcare facility that may be connected to the neural network. In certain examples, the neural network outputs data that is buffered (e.g., via the cloud, etc.) and validated before it is provided to another process.

Deep learning machines using convolutional neural networks (CNNs) may be used for image analysis. Stages of CNN analysis may be used for facial recognition in natural images, computer-aided diagnosis (CAD), etc.

Medical image data may be acquired using imaging modalities, such as magnetic resonance imaging (MRI). Medical image quality is often not affected by the machines producing the image but the patient. A patient moving during an MRI may create a blurry or distorted image that may prevent accurate diagnosis, for example.

Interpretation of medical images, regardless of quality, is only a recent development. Medical images are largely interpreted by physicians, but these interpretations may be subjective, affected by the condition of the physician's experience in the field and/or fatigue. Image analysis via machine learning may help steam-line a healthcare practitioner's workflow.

Deep learning machines may provide computer aided detection support to improve their image analysis with respect to image quality and classification, for example. However, issues faced by deep learning machines when applied to the medical field often lead to numerous false classifications. For example, deep learning machines need to overcome small training datasets and repetitive adjustments.

Deep learning machines, with minimal training, may be used to determine the quality of a medical image, for example. Semi-supervised and unsupervised deep learning machines may be used to quantitatively measure qualitative aspects of images. For example, deep learning machines may be utilized after an image has been acquired to determine if the quality of the image is enough for diagnosis. Supervised deep learning machines may also be used for computer aided diagnosis. Supervised learning may help reduce susceptibility to false classification, for example. These deep learning machines may improve computer aided diagnosis over time through training and transfer learning.

According to an aspect of the disclosure as shown in FIG. 3, a fully sampled reference k-space data (310) containing the entire k-space data may be acquired and an accelerated image containing only the partial k-space may be acquired. Further, the accelerated partial k-space may be grafted with the fully sampled reference k-space data (310) to generate an accelerated image data (320). The accelerate image data (320) and the fully sampled reference k-space data (310) may be inputted to an artifact prediction network (330). The artifact prediction network (330) may be a deep learning (DL) network. According to an aspect of the disclosure the artifact prediction network (330) may employ a dual regularized and self-adaptive smart loss function (331). The artifact prediction network (330) may predict the grafting artifacts using the smart loss function (331). Predicting the grafting artifact includes comparing the grafted data (320) with the fully sampled reference k-space data (310) using the smart loss function (331). Providing the fully sampled reference k-space data (310) as an additional channel along with the grafted data (320) and processing these images by dual regularized self-adaptive loss function may more accurately predict the grafting artifacts. The sharp high frequency artifacts may be removed by the DL module that uses fully sampled reference k-space data (310) and the grafted data (320). These artifacts may not be removed by the DL module that is trained using only the grafted data (320).

Loss functions used in the conventional DL modules assign fixed weight to regularization terms at the beginning of the computation. However, the smart loss function according to an aspect of the present disclosure is a dynamic smart loss function that may be configured to change the weights assigned to the regularization terms based on the relevance of the regularization term as the training progresses. In one example, the regularization weights for the loss terms are modulated based on the training loss after each epoch. A transfer function may be employed by the artefact prediction network to decide the regularization weights for loss function components. Loss function components may include the structural similarity index measure (SSIM) loss, perceptual (e.g. latent features based) loss, the mean absolute error (MAE) loss that may be dynamically adjusted for better image quality as the training progresses.

In one example, the higher usage of the SSIM in the beginning may lead to the fine banding artifacts in the MR images. However, use of the dynamic regularization approach according to an aspect of the disclosure may control the role of the SSIM in the loss function through the training. As predictions gets closer to the ground truth, more weight may be yielded to the SSIM. Further, the regularizer weights after each epoch may be updated by the transfer function. In one exemplary embodiment of the present disclosure, the smart loss function calculation may be based on the following formula:

$$\mathcal{L} = \alpha \times MAE + (1-\alpha) \times (1-SSIM)$$

The MAE may be computed on the predicted residue and the SSIM may be computed between the ground truth and artifact corrected image. The weights of the regularizer, $\alpha$, may be updated after each epoch depending on the MAE and SSIM values. As the prediction gets closer to the ground truth, the weightage to the SSIM loss may be increased. Further, the user may decide how soon the weightage to the SSIM starts increasing. According to the dynamic regularization method of the present disclosure, weights of the regularizer ($\alpha$) may be adjusted dynamically using the formula:

$$\alpha(r_m) = 1 - \frac{1}{1 + e^{-0.1(r_m - R)}} \text{ where } r_m = \frac{SSIM}{MAE}$$

and R is the ratio shift term which decides the nature of the curve to obtain the value of $\alpha$ corresponding to $r_m$. Higher value of R indicates larger role of the SSIM.

Figure 4:
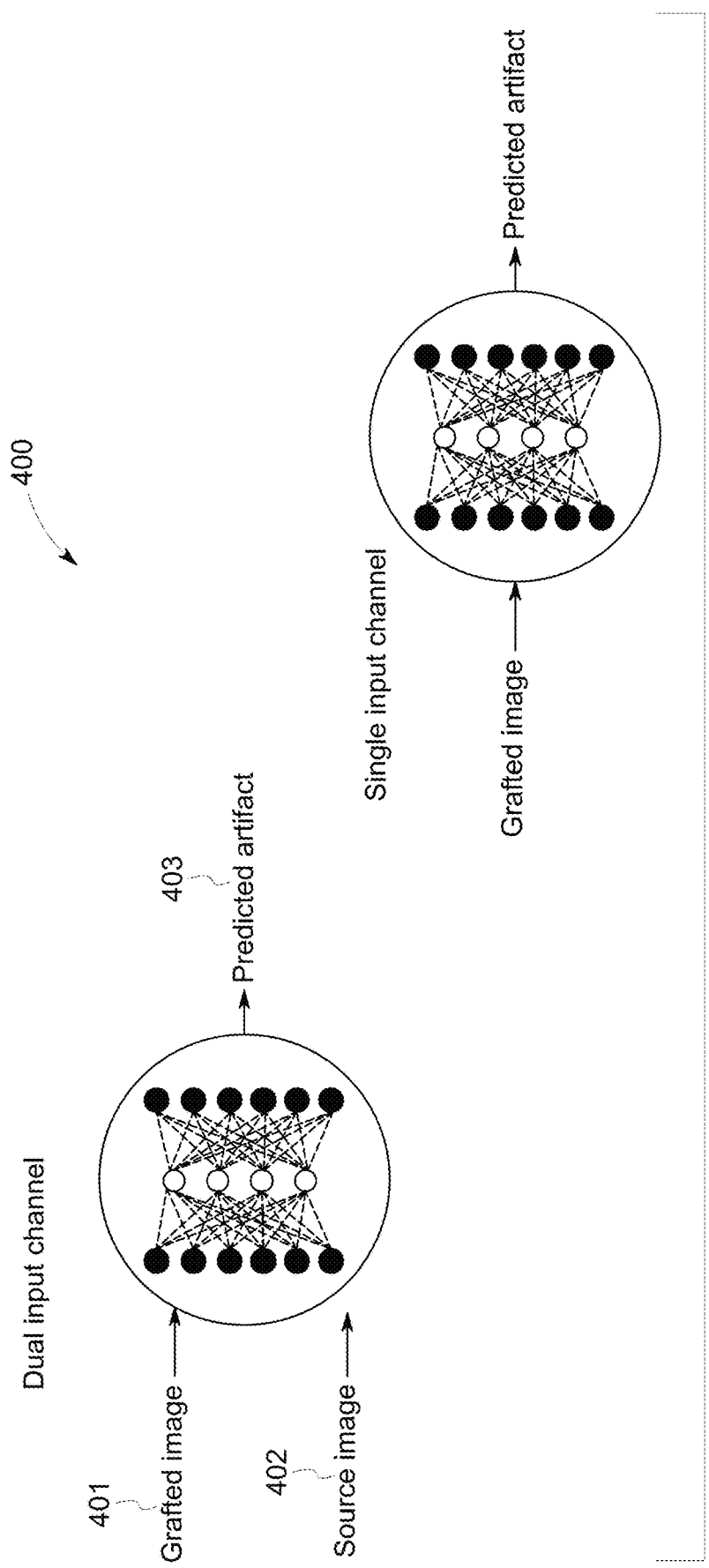
FIG. 4 illustrates a deep learning module trained using the dual input channel for predicting artifacts according to an aspect of the disclosure.

The method of the present disclosure accelerates the MRI examination thus the time saved using this method could be used to obtain higher resolution images for multiple contrasts. This method may be more efficient for acquiring the high-resolution data for multiple contrasts. According to an aspect of the disclosure, FIG. 4 shows a deep learning (DL) module trained using the dual input channel for predicting the artifacts. The DL module may be trained using only the grafted data (401) and using both the fully sampled reference k-space data (402) and the grafted data (dual input) (401) to analyze and predict (403) the artifact removal efficiency of the DL module. It may be seen that the artifact removal by the DL module is improved when the dual input was provided. It may be seen that the visual information fidelity (VIF) and the structural similarity index metric (SSIM) for the output were improved in case of the dual input models.

parison. Structural integrity of the images may be lost due to using only the partial k-space (520) with the artifacts (521) for training the DL module.

According to an aspect of the disclosure, when the partial k-space (520) is grafted with the fully sampled reference k-space data (510), the grafted data (530) has improved structural integrity and does not have the under sampling artifacts (521). In presence of the artifacts (521) in the partial k-space (520), the DL module may not be able to recover the complete structural integrity. Grafting however makes the DL correction possible even for the higher levels of acceleration. Accordingly, the process of grafting may remove the artifacts (521) to provide a data (530) with the improved image quality.

Figure 6:
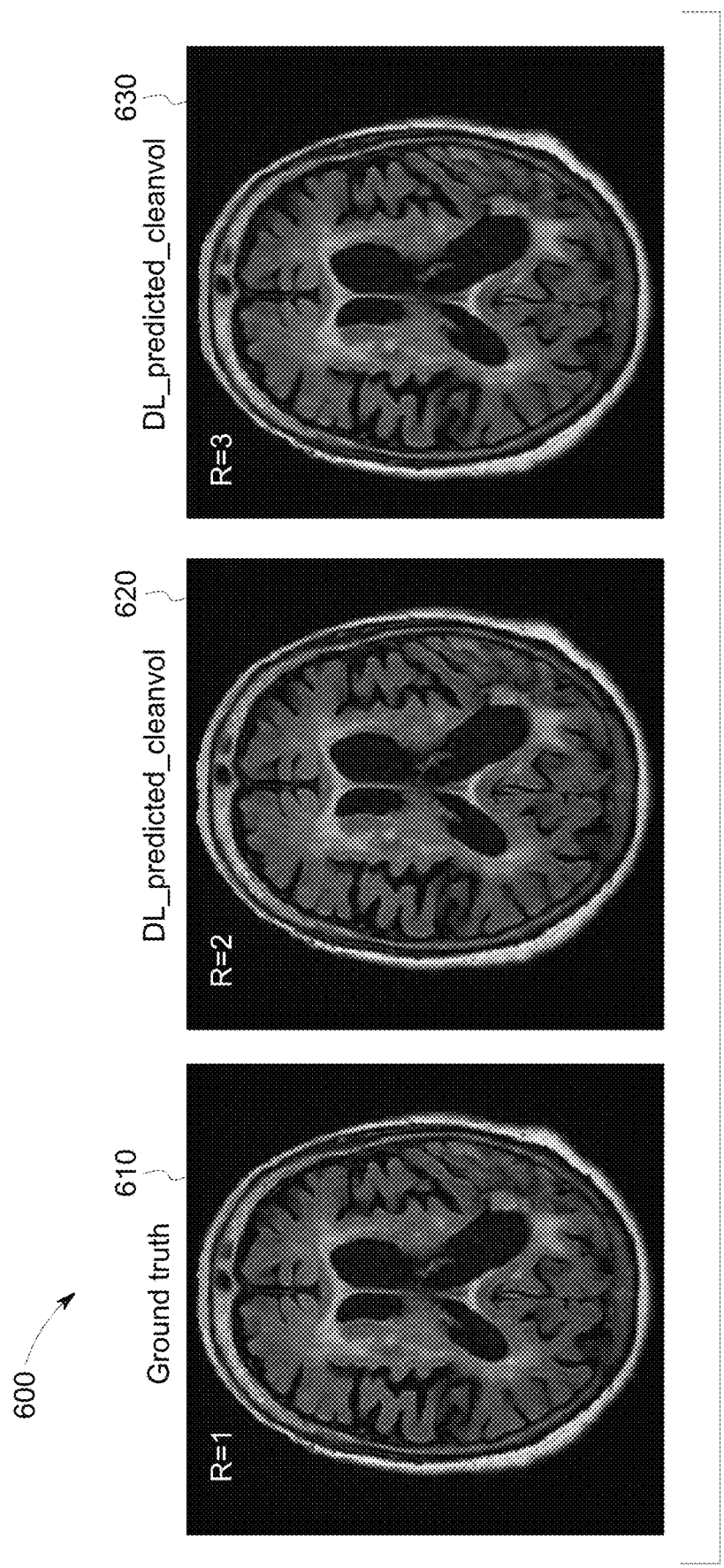
FIG. 6 illustrates a fully sampled reference image, a grafted image and an artifact corrected image generated by the DL module according to an aspect of the disclosure.

According to an aspect of the disclosure, FIG. 6 shows an example of the image data obtain using the MRI system. This data may include a fully sampled reference k-space data (610), a grafted data (620) and an artifact corrected data (630) generated by the DL module that is trained using the fully sampled reference k-space data (610) and the grafted data (620). It may be seen that the grafted data (620) may have the grafting artifacts and if the DL module is trained using only the grafted data (620), the DL module may not be able detect these artifacts during the further analysis of the subsequent images presented to the DL module. According to an aspect of the disclosure, when the DL module is trained using both the fully sampled reference k-space data (610) and the grafted data (620), the grafting artifacts such as sharp high frequency artifacts may be removed to generate an artifact corrected data (630).

Figure 7:
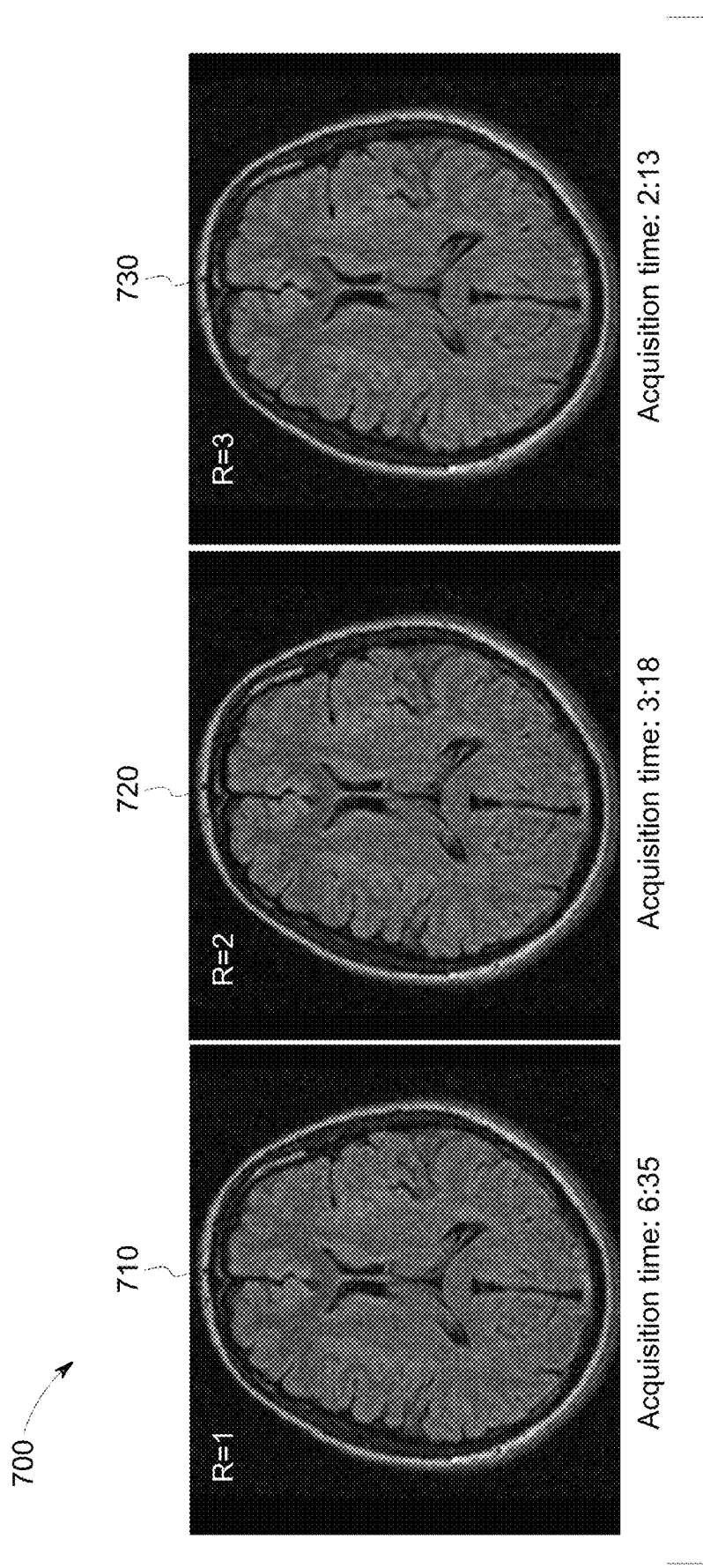
FIG. 7 illustrates an exemplary accelerated examination by magnetic resonance imaging (MRI) system according to an aspect of the disclosure.

According to an aspect of the disclosure, FIG. 7 shows an example of the accelerated examination by the magnetic resonance imaging (MRI) system. The fully sampled reference k-space data (710) acquired using the exemplary MRI system may take approximately up to six minutes and thirty-five seconds. This data (710) may be used as the reference k-space data to represent the ground truth. The partial k-space (720) represents only the central k-space acquired according to an aspect on the disclosure. In one example, the partial k-space (720) may be acquired in approximately three minutes and eighteen seconds. This partial k-space (720) and subsequently obtained k-space may be grafted with the complete k-space data stored on the computer memory to obtain the grafted k-space (720). Similarly, an accelerated k-space (730) may be obtained using the partially acquired k-space data and grafting the

| Models | VIF Mean | VIF std | pSNR mean | pSNR std | SSIM mean | SSIM std |
|---|---|---|---|---|---|---|
| Dual input | 0.672 | 0.032 | 36.325 | 2.099 | 0.962 | 0.042 |
| Single input | 0.659 | 0.045 | 35.554 | 2.157 | 0.957 | 0.051 |

Figure 5:
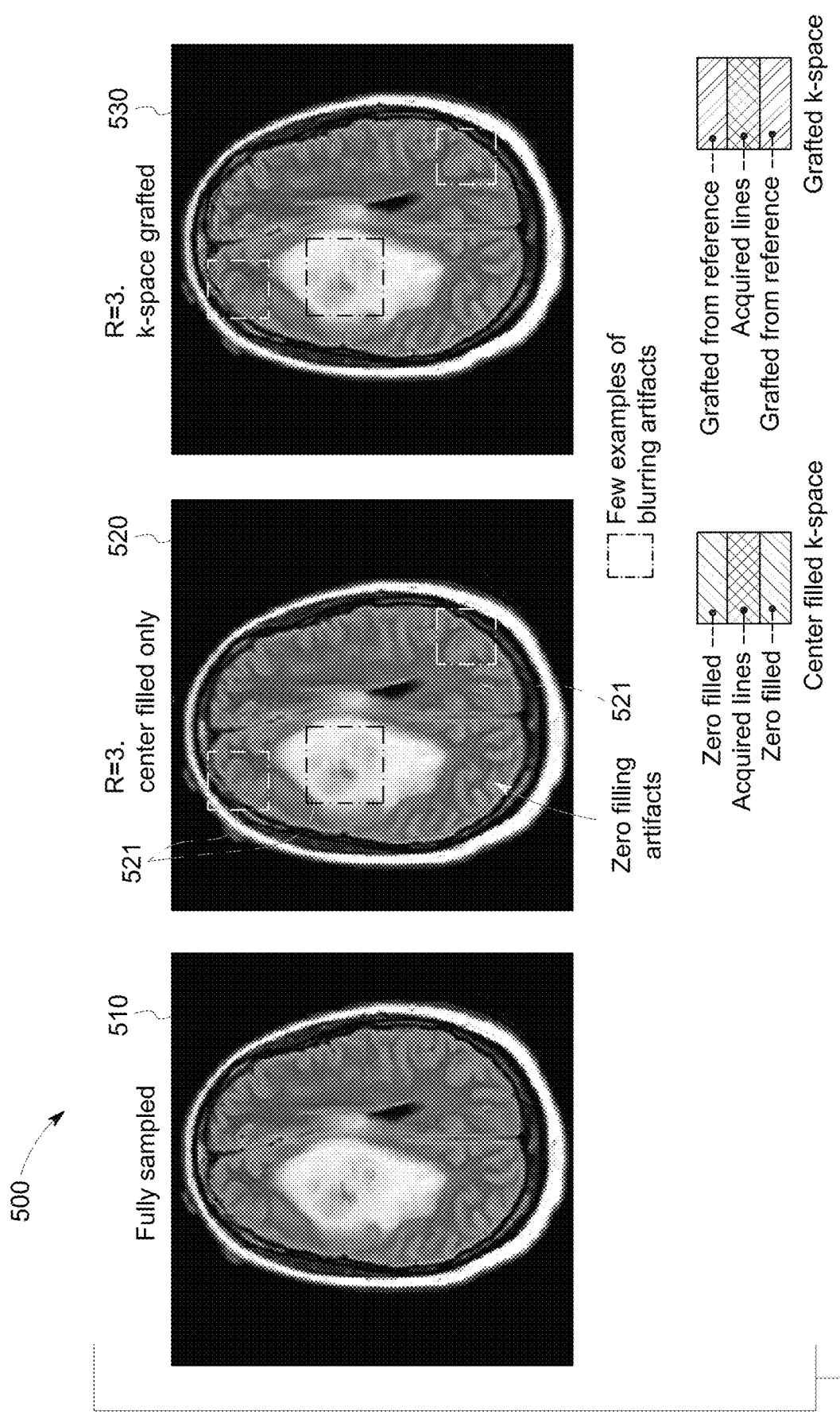
FIG. 5 illustrates an example k-space grafted MRI image according to an aspect of the disclosure.

According to an aspect of the disclosure, FIG. 5 shows fully sampled reference k-space data (510) and partial k-space (520) that may be obtained. The partial k-space (520) may be grafted with the fully sampled reference k-space data (510) to obtain the grafted k-space (530). According to an aspect of the disclosure, if the partial k-space (520) has artifacts (521), the deep learning module trained using the partial k-space (520) may be not be able to identify these artifacts (521). In one example, if the artifact such as blurring (521) present in the partial k-space (520) as shown in FIG. 5 are used to train the DL module, the DL module may not identify these image artifact (521) for all the images that may be presented to the DL module for compartial k-space data with the reference k-space data to generate an accelerated k-space data (730). Approximate time required for obtaining this grafted image may be up to two minutes and thirteen seconds. Improvement in time taken to acquire the MR images has significant impact on the image quality. Shorter duration of the image acquisition minimizes the motion artifacts caused by the movement of the patient organs such as lungs, heart and blood vessels. The acceleration in MR imaging according to an aspect of the disclosure reduces the data redundancy in the k-space data processing. The high-resolution isotropic images for multiple contrasts may be obtained in a single examination with the reduced net imaging time.

Figure 8:
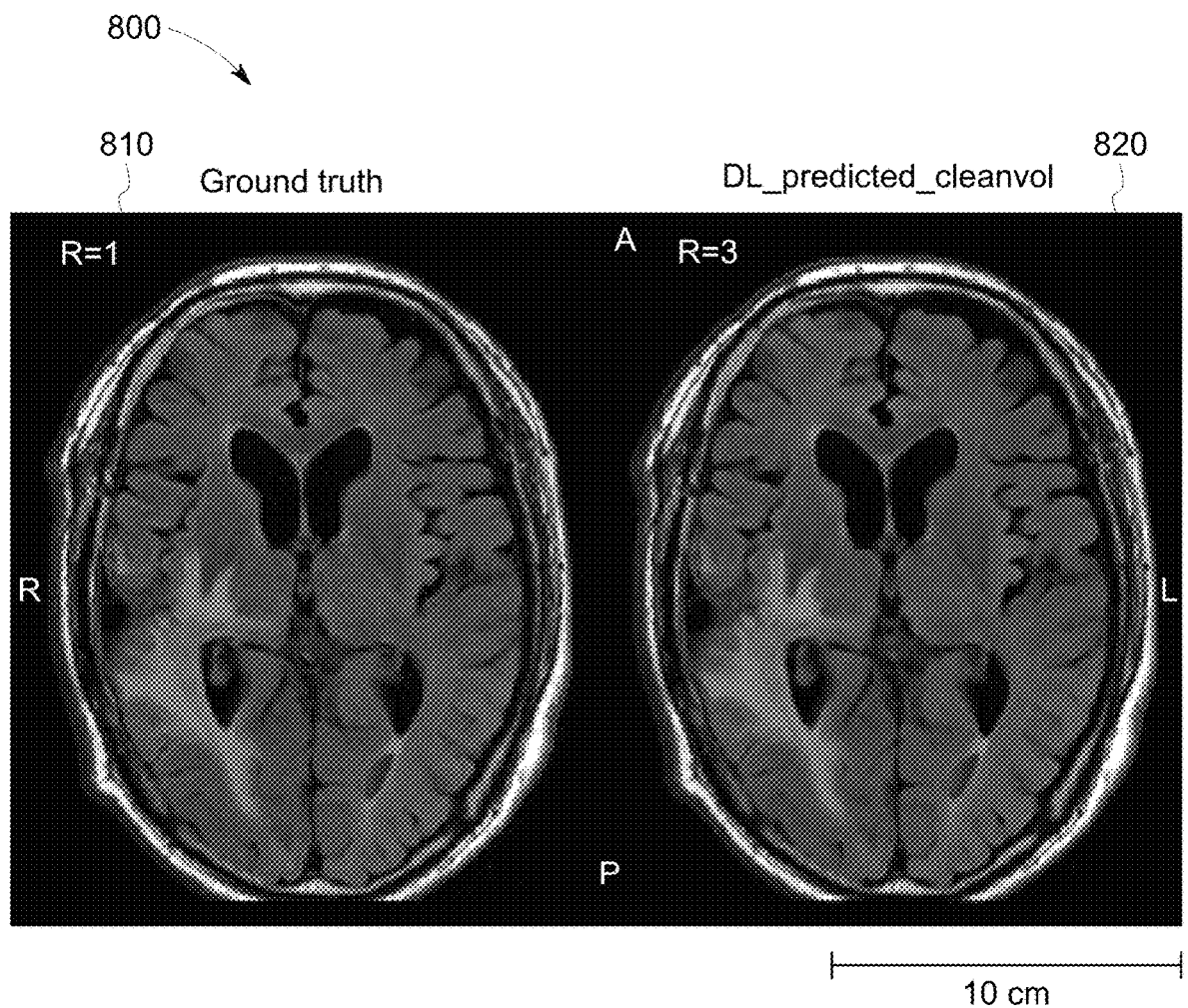
FIG. 8 illustrates an exemplary grafted image without artifacts generated by the DL module according to an aspect of the disclosure.

According to an aspect of the disclosure, FIG. 8 shows an example grafted image (820) without the artifacts generated by the DL module that is trained using both the fully sampled reference k-space data and the grafted data. The grafted data (820) as seen from FIG. 8 shows removal of the grafting artifacts and reduced image acquisition time. The method according to the present disclosure not only accelerates the MR imaging but also allows generation of the high-quality images by acquisition of the high-resolution data for multiple contrasts. Grafting allows preserving enough structure for the DL module to correct the accelerated data and offers easy scalability across the segments and the applications.

Figure 9:
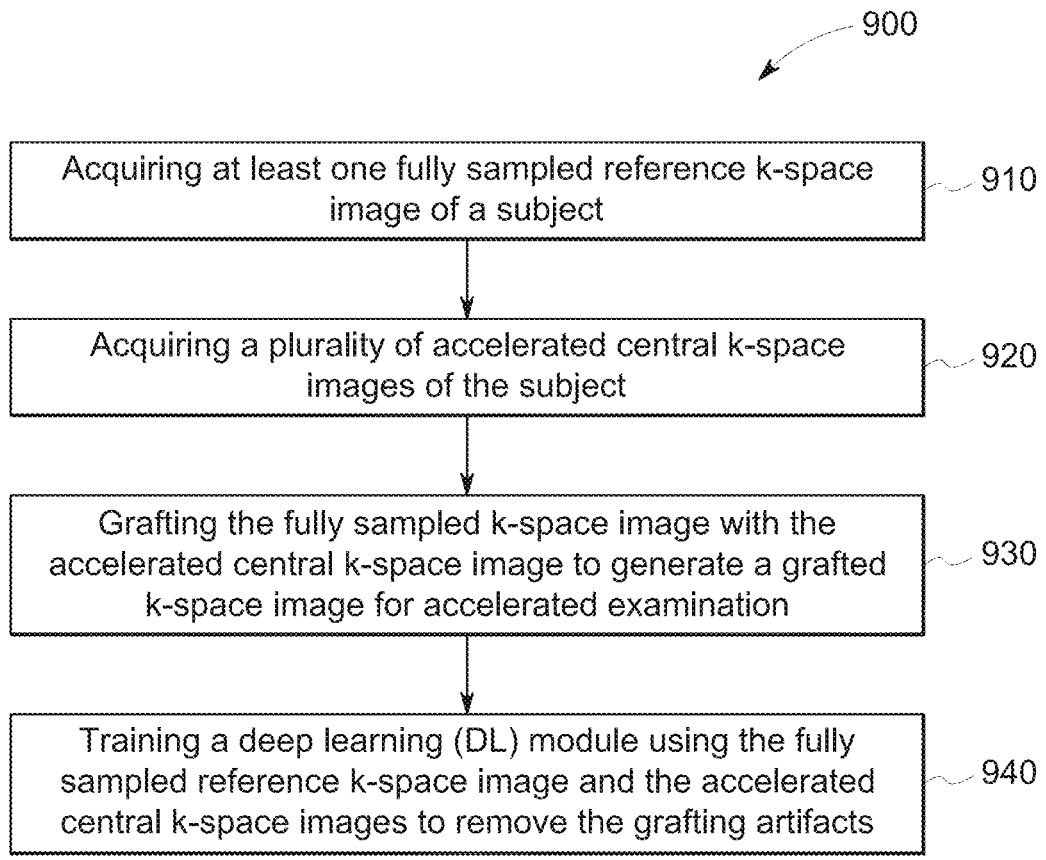
FIG. 9 illustrates a method of deep learning based magnetic resonance imaging (MRI) examination acceleration according to an aspect of the disclosure.

According to an aspect of the disclosure, FIG. 9 shows a method (900) of deep learning (DL) based magnetic resonance imaging (MRI) examination acceleration. The method (900) includes acquiring (910) at least one fully sampled reference k-space data of a subject using the magnetic resonance imaging (MRI) system. The method (900) further includes acquiring (920) a plurality of accelerated partial k-space of the subject by the MRI system. The method (900) further includes grafting (930) the partial k-space with the fully sampled reference k-space data to generate a grafted k-space for accelerated examination of the subject. The process of grafting (930) may be employed before processing the partial k-space by the DL module. The grafting (930) process may generate the artifacts such as the sharp high frequency artifacts that may be removed using a deep learning network according to an aspect of the disclosure. The method (900) further comprises training (940) a deep learning (DL) module using the fully sampled reference k-space data and the grafted data to remove the grafting artifacts.

In accordance with an aspect of the disclosure, training (940) the deep learning (DL) module may include inputting the grafted k-space and the reference k-space to an artifact prediction network. The artifact prediction network may be a deep learning (DL) network. According to an aspect of the disclosure the artifact prediction network may employ a dual regularized and self-adaptive smart loss function. The artifact prediction network may predict the grafting artifacts using the smart loss function. Predicting the grafting artifact includes comparing the grafted image with the fully sampled image using the smart loss function. Providing the fully sampled reference k-space data as an additional channel along with the grafted data and processing these images by the dual regularized self-adaptive smart loss function may accurately predict the grafting artifacts. The sharp high frequency artifacts may be removed by the DL module that uses fully sampled k-space data and grafted data. These artifacts may not be removed by the DL module that is trained using only the grafted data.

Loss functions used in the conventional DL modules assign fixed weight to the regularization terms at the beginning of the computation. However, the smart loss function according to an aspect of the present disclosure is dynamic and configured to change the weights assigned to the regularization terms based on the relevance of the regularization term as the training progresses. In one example, the regularization weights for the loss terms may be modulated based on the training loss after each epoch. A transfer function may be employed by the artefact prediction network to decide the regularization weights for loss function components. The loss function components may include the structural similarity index measure (SSIM) loss, perceptual (e.g. latent features based) loss, the mean absolute error (MAE) loss that may be dynamically adjusted for better image quality as the training progresses.

In one example, the higher usage of the SSIM in the beginning may lead to the fine banding artifacts in the MR images. However, use of the dynamic regularization approach according to an aspect of the disclosure may control the role of the SSIM in the loss function through the training. As the predictions get closer to the ground truth, more weight may be yielded to the SSIM. Further, the regularizer weights after each epoch may be updated by the transfer function. The smart loss function calculation may be based on the following formula:

$$\mathcal{L} = \alpha \times \text{MAE} + (1-\alpha) \times (1-\text{SSIM})$$

MAE may be computed on the predicted residue and the SSIM may be computed between the ground truth and the artifact corrected image. The weights of the regularizer, $\alpha$, may be updated after each epoch depending on the MAE and the SSIM values. As the prediction gets closer to the ground truth, weightage to the SSIM loss may be increased. Further, the user may decide how soon the weightage to the SSIM starts increasing. According to the dynamic regularization method of the present disclosure, weights of the regularizer ($\alpha$) may be adjusted dynamically using the formula:

$$\alpha(r_m) = 1 - \frac{1}{1 + e^{-0.1(r_m - R)}} \text{ where } r_m = \frac{SSIM}{MAE}$$

and R is the ratio shift term which decides the nature of the curve to obtain the value of $\alpha$ corresponding to $r_m$. Higher value of R indicates larger role of the SSIM.

The method (900) of the present disclosure not only accelerates the MRI examination but also provides the images with improved resolution. This method (900) may be more efficient in for acquiring the high-resolution data for multiple contrasts. According to an aspect of the disclosure, the deep learning (DL) module trained using the dual input channel may have better artifact predicting capabilities than the DL module trained using the single channel images. The DL module may be trained using only the grafted data (single input) and using both the reference data and the grafted data (dual input) to analyze and predict the artifact removal efficiency of the DL module. It may be seen that the artifact removal by the DL module is improved when the dual input was provided. It may be seen that the visual information fidelity (VIF) and the structural similarity index metric (SSIM) of output were improved in case of the dual input models.

This written description uses examples to disclose the invention, including the best mode, and to enable any person skilled in the art to practice the invention, including making and using any computing system or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

The invention claimed is:

1. A method of magnetic resonance imaging (MRI) examination acceleration, the method comprising:
acquiring at least one fully sampled reference k-space data of a subject;
acquiring a plurality of partial k-space data of the subject;

grafting the plurality of partial k-space data with the at least one fully sampled reference k-space data to generate a grafted k-space data for accelerated examination; and wherein grafting the plurality of partial k-space data with the fully sampled k-space data is carried out before a deep learning (DL) module-based reconstruction of the grafted data.

2. The method of claim 1 wherein subsequent scanning comprises acquiring only a set of partial k-space data of the subject and grafting the set of partial k-space data with the fully sampled k-space data to generate the grafted k-space data for accelerated examination.

3. The method of claim 1 wherein grafting the plurality of partial k-space data with the fully sampled reference k-space data comprises grafting a missing structural information in the plurality of partial k-space data from the at least one fully sampled reference k-space data.

4. The method of claim 1, wherein grafting the plurality of partial k-space data with the fully sampled k-space data before the deep learning (DL) module-based reconstruction of the grafted data provides structural information to the deep learning (DL) module to correct grafting artifacts.

5. The method of claim 1 wherein the plurality of partial k-space data comprises k-space data for multiple protocol.

6. The method of claim 1 wherein the plurality of partial k-space data comprises central k-space data and a peripheral portion k-space data.

7. The method of claim 1 wherein a smart loss function of the DL module comprises a plurality of regularization terms and the smart loss function is configured to change a weight assigned to the plurality of regularization terms based on a relevance of the regularization term during training of the DL module.

8. A method of deep learning (DL) based magnetic resonance imaging (MRI) examination acceleration, the method comprising:
acquiring at least one fully sampled reference k-space data of a subject;
acquiring a plurality of partial k-space data of the subject;
grafting the plurality of partial k-space data with the at least one fully sampled reference k-space data to generate a grafted data for accelerated examination; and
training a deep learning (DL) module using the grafted data and the fully sampled reference k-space data to remove grafting artifacts.

9. The method of claim 8 wherein the deep learning (DL) module comprises a smart loss function.

10. The method of claim 9 wherein the smart loss function comprises a plurality of regularization terms and the smart loss function is configured to change a weight assigned to the plurality of regularization terms based on a relevance of the regularization term during training of the deep learning (DL) module.

11. The method of claim 10 wherein the weights assigned to the each of the regularization terms is dynamically modulated based on a training loss after each imaging epoch.

12. The method of claim 11 wherein dynamically modulating the regularization terms include modulating a structural similarity index measure (SSIM) loss, perceptual loss and a mean absolute error (MAE) loss.

13. The method of claim 9 wherein the smart loss function is defined as:
$$\mathcal{L} = \alpha \times MAE + (1-\alpha) \times (1-SSIM)$$
wherein $\mathcal{L}$ represent smart loss;
MAE is mean absolute error;
SSIM is structural similarity index measure; and
$\alpha$ is weight of the regularizer;
wherein $\alpha$ is updated after each epoch depending on the MAE and SSIM values.

14. The method of claim 8 further comprising acquiring a plurality of MRI images comprising a simultaneous multi-slice reading for accelerated examination.

15. A magnetic resonance imaging (MRI) system comprising:
at least one radiofrequency (RF) body coil adapted to transmit and receive radiofrequency (RF) signals to and from a subject;
a transceiver module configured to digitize the signals received by the radiofrequency (RF) body coil;
a control system configured to process the digitized signals and generate a k-space data corresponding to an imaged volume of the subject, wherein the MRI system is configured to acquire fully sampled reference k-space data of the subject and a plurality of partial k-space data of the subject;
a computer processor configured to graft the plurality of partial k-space data of the subject with the fully sampled reference k-space data of the subject to generate a grafted k-space data for accelerated examination; and
wherein the MRI system further comprises a deep learning (DL) module employed on a computer memory, wherein the deep learning (DL) module is trained using the fully sampled reference k-space data and the grafted k-space data.

16. The magnetic resonance imaging (MRI) system of claim 15, wherein the deep learning module is an artifact prediction network comprising a smart loss function.

17. The magnetic resonance imaging (MRI) system of claim 16, wherein the smart loss function comprises a plurality of regularization terms and the smart loss function is configured to change a weight assigned to the each of the plurality of the regularization terms based on a relevance of the regularization term during training of the deep learning (DL) module.

18. The magnetic resonance imaging (MRI) system of claim 17 wherein the weights assigned to the each of the regularization terms is dynamically modulated based on a training loss after each imaging epoch.

19. The magnetic resonance imaging (MRI) system of claim 18 wherein dynamically modulating the regularization terms include modulating a structural similarity index measure (SSIM) loss, perceptual loss, and a mean absolute error (MAE) loss.

20. The magnetic resonance imaging (MRI) system of claim 15 wherein the computer processor is configured to graft the plurality of partial k-space data of the subject with the fully sampled reference k-space data of the subject before the deep learning (DL) module-based reconstruction of the grafted data.

21. The magnetic resonance imaging (MRI) system of claim 15 wherein the MRI system is configured to acquire a plurality of MRI images comprising a simultaneous multi-slice reading for accelerated examination.

* * * * *